United States Patent [19]
Fernandez et al.

[11] 3,958,563
[45] May 25, 1976

[54] TWO SPEED SYSTEM FOR EEG RECORDING

[76] Inventors: Heriberto Fernandez, 1822 Gaston St., Winston-Salem, N.C. 27103; George T. Pardue, P.O. Box 131, Pilot Mountain, N.C. 27041

[22] Filed: Nov. 6, 1974

[21] Appl. No.: 521,401

[52] U.S. Cl. ..................... 128/2.1 B; 346/33 ME
[51] Int. Cl.² ......................................... A61B 5/04
[58] Field of Search ........ 128/2.1 B, 2.1 M, 2.06 G, 128/2.06 A, 2.06 F, 2.06 R; 346/33 ME; 328/148

[56] References Cited
UNITED STATES PATENTS

| | | | |
|---|---|---|---|
| 3,513,834 | 5/1970 | Suzuki et al. | 128/2.1 B |
| 3,646,930 | 3/1972 | Patterson et al. | 128/2.06 F |
| 3,650,263 | 3/1972 | Kowalski | 128/2.06 G |
| 3,721,230 | 3/1973 | Zienicki | 128/2.1 B |
| 3,824,990 | 7/1974 | Baule | 128/2.06 G |
| 3,841,309 | 10/1974 | Salter et al. | 128/2.1 B |
| 3,841,315 | 10/1974 | Kopp | 128/2.06 F |
| 3,854,472 | 12/1974 | Giori | 128/2.06 A |

FOREIGN PATENTS OR APPLICATIONS

| | | | |
|---|---|---|---|
| 1,962,077 | 11/1969 | Germany | 128/2.06 A |
| 911,078 | 11/1962 | United Kingdom | 128/2.06 A |
| 1,202,869 | 8/1970 | United Kingdom | 128/2.06 A |

*Primary Examiner*—William E. Kamm
*Assistant Examiner*—Lee S. Cohen
*Attorney, Agent, or Firm*—Cushman, Darby & Cushman

[57] ABSTRACT

A method and system for recording EEG waveforms whereby the amplitude of the waveform signal in both positive and negative direction is compared with variable levels and a trigger signal produced when the amplitude exceeds a level to cause the strip of recording paper to speed up for at least a predetermined time and to continue for the length of the seizure so that little paper is accumulated during periods of uninteresting activity while a complete readable record is produced of any notable EEG activity, such as an epileptic seizure.

16 Claims, 1 Drawing Figure

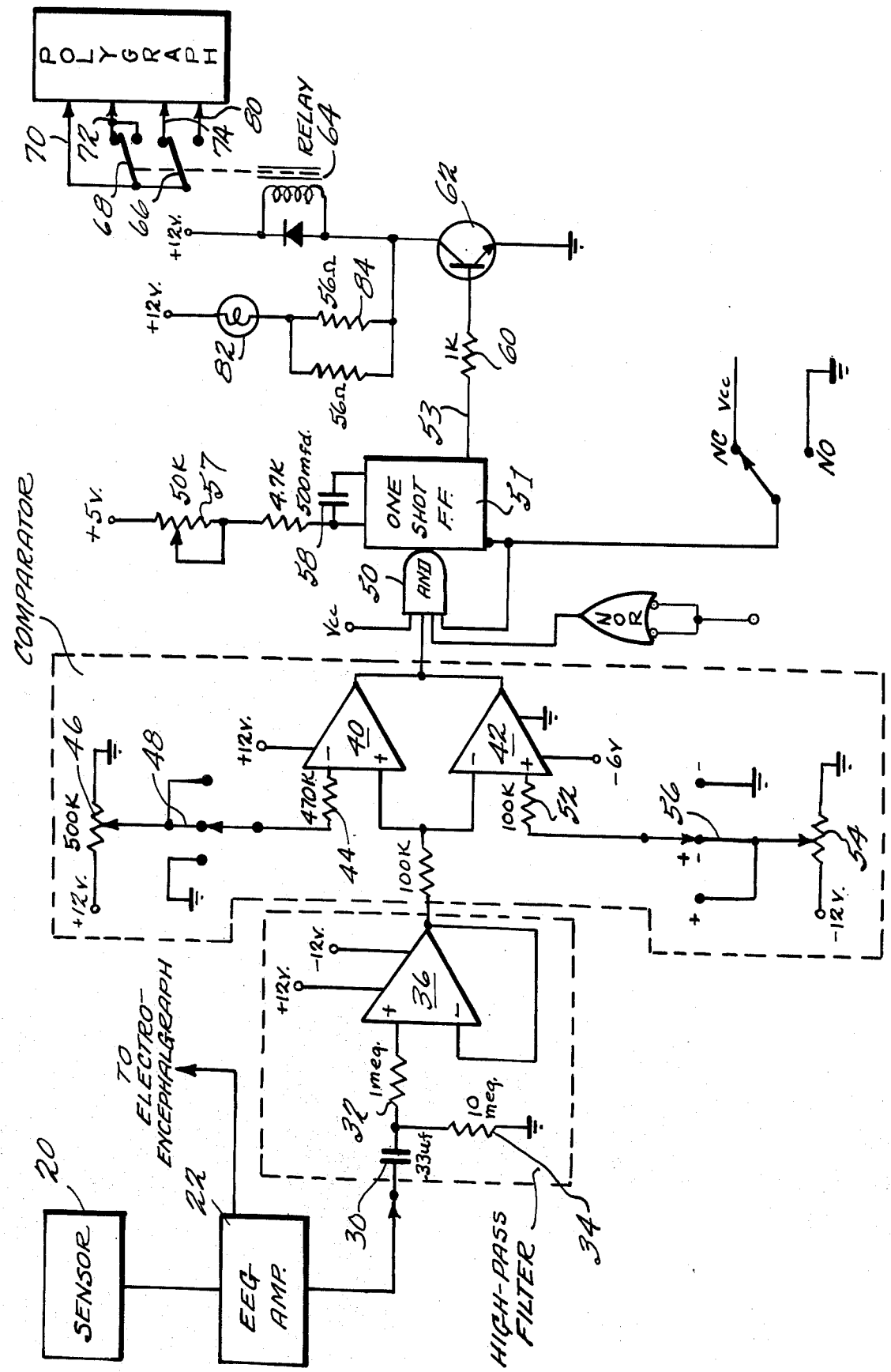

TWO SPEED SYSTEM FOR EEG RECORDING

BRIEF DESCRIPTION OF THE PRIOR ART AND SUMMARY OF THE INVENTION

The invention relates to a method and system for recording EEG waveforms.

The polygraph is a medical instrument which has found increasing use in recent years as a diagnostic tool for use in recording body waveforms such as EKG waveforms from the heart and EEG waveforms from the brain. Particularly with regard to the latter signals, it is often useful to continuously record EEG waveforms of an epileptic in order to record the EEG waveforms which are produced during a seizure. These seizure waveforms, fortunately for the epileptic, are infrequent and, accordingly, when continuously monitoring, the physician is normally faced at the end of a monitoring period with a vast stack of paper which must be scanned and analyzed. Most of this stack represents time intervals in which no interesting waveforms were being produced. Accordingly, not only is the paper recording this uninteresting information totally wasted but a great deal of time and effort is required for the physician to wade through this useless information.

The present invention relates to a system and method for use with a conventional electroencephalograph for recording electrical body waveforms and particularly for recording EEG waveforms whereby the speed at which the strip of paper is driven in the electroencephalograph is shifted from a relatively low speed to a high speed upon detection of the advent of a period of activity which is desired to be considered. Epileptic seizures are characterized by spikes of relatively high amplitude in the EEG waveform. According to one aspect of the invention of this application, a trigger signal is produced when the amplitude of the EEG waveform in either the positive or the negative direction exceeds a predetermined preset level. This trigger signal in turn causes the drive for the electroencephalograph to be speeded up for at least a predetermined period, for example four seconds, and to continue at the higher speed for the duration of the seizure. Thus the machine saves up to 80% of the paper which would otherwise be used for recording continuously at the higher speed and also the scanning time of the position is minimized because of the lower volume of the paper and because the period of the attacks stand out.

According to the specific embodiment illustrated in the drawing of this application and discussed in detail below, the amplified EEG waveform is applied to a high-pass filter which includes an operational amplifier and the output of this high-pass filter is in turn applied to a comparator circuit comprising two operational amplifiers, one producing an output trigger when the amplitude of the applied EEG signal exceeds a predetermined level with respect to some reference voltage, for example ground, in the positive direction, while the other produces a trigger voltage when the amplitude of the applied EEG signal exceeds a predetermined level in the negative direction. These levels are each preferably provided by a variable resistor connected to one of the inputs of the differential operational amplifier. Switches are connected between each of the respective variable resistors and the respective inputs to the differential operational amplifiers so that the circuitry can be easily switched to respond only to positive or negative excursions.

The outputs of the two operational differential amplifiers are in turn applied by a conventional logic to a one-shot flip-flop or multivibrator which produces an output signal having a duration which can be varied by a connected variable resistor. The output of the flip-flop is in turn connected to a relay circuit which shiifts the electrical connections to a conventional electroencephalograph to vary the speed of the strip of paper, for example, from a low speed of 3.0 mm/second to a fast speed of 30 mm/second with the latter speed being a typical recording speed for EEG waveforms. It has been found that the transition between the lower and the higher speed can be successfully made without producing any distortion in the EEG recorded waveform.

Many other objects and purposes of the invention will be clear from the following detailed description of the drawing.

BRIEF DESCRIPTION OF THE DRAWINGS

The FIGURE illustrates, partially in block diagram, one embodiment of the system of this invention.

DETAILED DESCRIPTION OF THE DRAWING

Reference is now made to the drawing which illustrates one embodiment of the unique EEG recording system of this invention. EEG signals from the brain of an epileptic patient or other person whose brain waves are to be monitored are conventionally detected by a conventional sensor 20 and the resultant electrical signal conventionally amplified by ab EEG amplifier 22 of the type normally found in electroencephalographs. The output of the EEG amplifier 22 is of course applied to the writing pens of the electroencephalograph to record on a strip of paper moving past a set of pens the electric signal produced by amplifier 22 and accordingly the EEG waveform.

The output of EEG amplifier 22 is also applied to the unique circuit of this invention which causes the speed of the paper in the electroencephalograph to vary as discussed generally above. The output of EEG amplifier 22 is applied to a high-pass filter comprising capacitor 30, resistor 32, resistor 34 and differential operational amplifier 36 which is connected as illustrated to form part of a high-pass filter. The filtered output of operational amplifier 36 is applied to the positive input of a further operational amplifier 40 and the negative input of another operational amplifier 42. Both operational amplifiers 40 and 42 are functioning in their differential mode which is to say that the signal which is produced at the output of operational amplifiers 40 and 42 represents the difference between the two input signals. The negative input of operational amplifier 40 is connected via resistor 44 to a variable resistor 46 via switch 48. Resistor 46 is connected to a positive voltage source and accordingly defines a positive level above a reference level, which in this embodiment is ground. This represents the trigger voltage. When the EEG waveform exceeds in amplitude the voltage defined by variable resistance 46 then a trigger signal is produced by operational amplifier 40 which is applied to AND-gate 50.

Similarly, the positive input to operational amplifier 42 is connected via resistor 52 to a variable resistor 54 which is in turn connected to a negative voltage and which defines the negative level below which excursions of the EEG waveform will produce a trigger signal. Switch 56 connects resistor 54 to the positive input of operational amplifier 42. Switches 48 and 56 can be shifted as illustrated so that the circuit will respond only to either positive or to negative excursions of the EEG waveform.

The output of operational amplifiers 40 and 42 is connected to a AND-gate 50 so that AND-gate 50 causes one-shot flip-flop 51 to shift its output condition at terminal 53 from a low to high output when either operational amplifier 40 or 42 produces a trigger signal. One-shot flip-flop 51 then produces a pulse having a duration which is determined by the resistance of variable resistance 57 which, together with capacitor 58, forms a timing circuit. A time duration of about 4 seconds has been found to be quite satisfactory. Terminal 53 is connected by resistor 60 to the base of transistor 62 while the collector of transistor 62 is connected via relay coil 64 to a positive voltage source so that when transistor 62 is shifted to its conductive state by the output of flip-flop 51, current flows through coil 64 causing its controlled switches 66 and 68 to shift from their illustrated positions. In the illustrated positions, lines 70 and 72 which are connected to the relay which controls the motor of the electroencephalograph are connected to one voltage line 74 by switch 66. When switches 66 and 68 are shifted from their illustrated position, lines 70 and 72 are then connected to line 80 which causes a voltage to be applied to the motor in the electroencephalograph to cause that motor to drive the strip at a much higher rate.

An indicator lamp 82 is also connected to the collector of transistor 62 via resistors 84 and 86 so as to provide an indication when the electroencephalograph is operating at the higher speed.

Many changes and modifications in the above-described embodiment of the invention can of course be carried out without departing from the scope thereof. Accordingly, that scope is intended to be limited only by the scope of the appended claims.

What is claimed is:

1. A system for recording EEG electrical body waveforms comprising:
   means for detecting an EEG waveform and producing an electrical signal representing said waveform,
   means for comparing the amplitude of said electrical signal with a predetermined amplitude level and producing a trigger signal when said amplitude of said electrical signal exceeds said predetermined level,
   means responsive to said electrical signal for producing a graphical representation of said waveform on a strip of recording material,
   means for driving said strip of recording material past said representation producing means, and
   means for causing said driving means to change the speed at which said recording material is driven from a first speed to a second speed higher than said first speed when said comparing and producing means produces said trigger signal.

2. A system as in claim 1 wherein said representation producing means is a polygraph.

3. A system as in claim 1 wherein said causing means includes means for maintaining said second speed for a predetermined time following said trigger signal.

4. A system as in claim 1 wherein said causing means includes a one-shot flip-flop means connected to said comparing means for shifting from a first to second electrical condition at an output upon receipt of said trigger signal for a predetermined time and relay means connected to said flip-flop means for applying a first voltage signal to said driving means when said flip-flop means is in said first condition and a second voltage signal to said driving means when said flip-flop means is in said second condition.

5. A system as in claim 4 further including means for varying said predetermined time.

6. A system as in claim 5 wherein said predetermined time is roughly 4 seconds.

7. A system as in claim 4 further including indicator means connected to said flip-flop means output for indicating when said flip-flop means is in said second condition and accordingly said driving means is driving said strip at said second speed.

8. A system as in claim 1 wherein said comparing and producing means includes means for establishing said amplitude level and an operational amplifier with one input connected to said detecting means for receiving said electrical signal and the othe input connected to said establishing means for receiving said amplitude level.

9. A system as in claim 8 wherein said establishing means includes a variable resistor connected to said other input and a voltage source connected to said variable resistor for applying a D.C. voltage to said other input.

10. A system as in claim 9 wherein said comparing means and producing means includes means for establishing a second amplitude level having a polarity opposite the first amplitude level and a second operational amplifier with one input connected to said detecting means for receiving said electrical signal and the other input connected to said second amplitude level establishing means for receiving said second amplitude level having a polarity opposite the first amplitude level.

11. A system as in claim 10 wherein said second amplitude level establishing means includes a second voltage source, and second variable resistor connected to said other input of said second amplifier and to said second voltage source, said second voltage source having a polarity opposite that of the voltage source connected to the first variable resistor, for applying a second D.C. voltage thereto.

12. A system as in claim 11 further including first switch means for connecting and disconnecting said first variable resistor from said other input of said first operational amplifier and second switch means for connecting and disconnecting said second variable resistor from said other input of said second operational amplifier.

13. A system as in claim 1 further including
   means for amplifying said electrical signal from the detecting means, and
   a high pass filter connected between said amplifying means and said comparing and producing means.

14. A system as in claim 1 wherein said strip is paper and said driving means includes a variable speed motor.

15. A system for recording EEG electrical body waveforms comprising:
   means for detecting an EEG signal and producing an electrical waveform signal,
   means connected to said detecting and producing means for producing a trigger signal when the amplitude of said waveform signal in at least one polarity exceeds a predetermined level with respect to a given reference,
   means responsive to said waveform signal for producing a graphical representation of said waveform on a strip of recording material, means for driving said strip past said representation producing means, and means for changing the speed at driving said strip for a predetermined time from a first speed to a second speed higher than said first speed upon production of said trigger signal.

16. A system as in claim 15 wherein said trigger signal means includes means for establishing a positive predetermined level and a negative predetermined level above and below, respectively, a reference level, and means for comparing the amplitude of said waveform signal with said positive and negative levels and producing said trigger signal when said amplitude of said waveform signal exceeds one of said positive and negative levels.

* * * * *